(12) United States Patent
Tyber et al.

(10) Patent No.: US 12,133,639 B1
(45) Date of Patent: Nov. 5, 2024

(54) INTERCHANGEABLE TOOL HANDLE

(71) Applicant: Tyber Medical LLC, Bethlehem, PA (US)

(72) Inventors: Jeffrey Tyber, Breinigsville, PA (US); Matthew Bellenoit, Northampton, PA (US); Matthew Atoulikian, Basking Ridge, NJ (US); Chandler Kline, Lancaster, PA (US); Christopher Faresich, Denville, NJ (US)

(73) Assignee: Tyber Medical LLC, Bethlehem, PA (US)

( * ) Notice: Subject to any disclaimer, the term of this patent is extended or adjusted under 35 U.S.C. 154(b) by 965 days.

(21) Appl. No.: 16/506,415

(22) Filed: Jul. 9, 2019

Related U.S. Application Data

(60) Provisional application No. 62/695,981, filed on Jul. 10, 2018.

(51) Int. Cl.
*A61B 17/00* (2006.01)

(52) U.S. Cl.
CPC ...... *A61B 17/00* (2013.01); *A61B 2017/0023* (2013.01); *A61B 2017/00464* (2013.01)

(58) Field of Classification Search
CPC ............ A61B 17/00; A61B 2017/0023; A61B 2017/00464
See application file for complete search history.

(56) References Cited

U.S. PATENT DOCUMENTS

| | | | | |
|---|---|---|---|---|
| 5,893,873 | A * | 4/1999 | Rader | A61B 17/2909 606/205 |
| 7,955,323 | B2 * | 6/2011 | Lechot | A61B 17/162 606/1 |
| 9,327,081 | B2 * | 5/2016 | Gobron | A61B 17/32056 |
| 2008/0086114 | A1 * | 4/2008 | Schmitz | A61B 17/1757 606/1 |
| 2014/0012236 | A1 * | 1/2014 | Williams | A61B 17/07207 606/1 |
| 2017/0151007 | A1 * | 6/2017 | Philipon | A61B 17/8888 |

FOREIGN PATENT DOCUMENTS

| | | | | |
|---|---|---|---|---|
| DE | 60023104 T2 | * | 7/2006 | ......... A61B 17/2909 |
| GB | 2466180 B | * | 7/2013 | ......... A61B 17/2909 |
| WO | WO-2017136710 A2 | * | 8/2017 | ......... A61B 17/2909 |

\* cited by examiner

*Primary Examiner* — Gary Jackson
*Assistant Examiner* — Ranjani Mari Sundaresan
(74) *Attorney, Agent, or Firm* — Joseph E. Maenner; Maenner & Associates, LLC

(57) ABSTRACT

A handle assembly includes an elongate body having a proximal end, a distal end, and a central longitudinal axis extending between the proximal end and the distal end. A side passage extends through the body transverse to the longitudinal axis and intersects the through-passage. A locking mechanism is located in the side passage and is configured to releasably retain a medical tool onto the assembly.

20 Claims, 12 Drawing Sheets

INTERCHANGEABLE TOOL HANDLE

CROSS-REFERENCE TO RELATED APPLICATION

The present application claims the benefit of U.S. Provisional Patent Application Ser. No. 62/695,981, filed on Jul. 10, 2018, which is incorporated herein by reference in its entirety.

BACKGROUND OF THE INVENTION

Field of the Invention

The present invention relates to an interchangeable tool handle that can be part of a kit with additional instruments that can accommodate multiple instruments from the kit.

Description of the Related Art

Throughout the course of a single medical procedure, such as, for example, insertion of an implant between two adjacent vertebrae, it may be necessary to use multiple tools provided in a single kit, with each tool having its own handle. Such tools increase both the size and cost of the kit.

It would be beneficial to provide a single use, disposable, and sterile handle assembly as part of a kit with additional instruments that can accommodate multiple different instruments from the kit.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a handle assembly that includes an elongate body having a proximal end, a distal end, and a central longitudinal axis extending between the proximal end and the distal end. A side passage extends through the body transverse to the longitudinal axis and intersects the through-passage. A locking mechanism is located in the side passage and is configured to releasably retain a medical tool onto the assembly.

In an alternative embodiment, the handle assembly further includes a retaining member that is adapted to engage the locking mechanism and retain the locking mechanism in the side passage.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
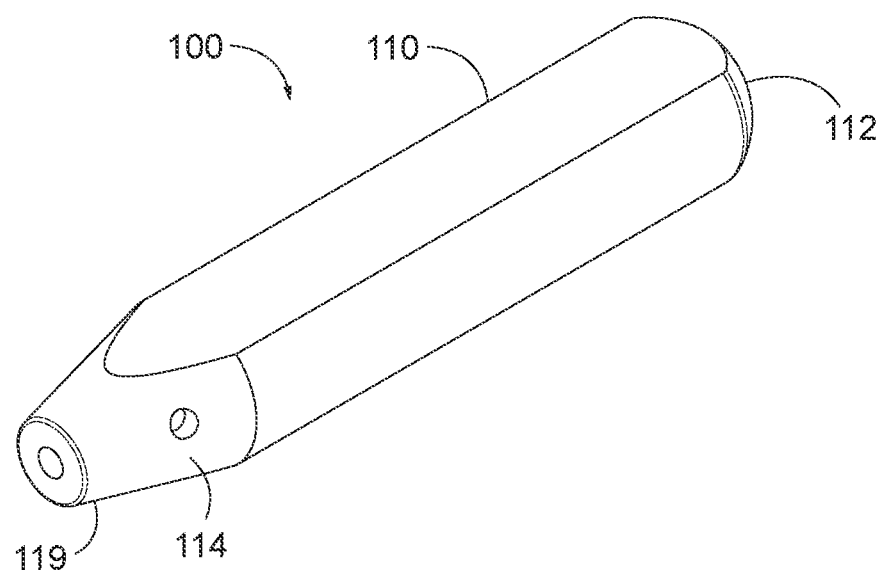
FIG. 1 is a perspective view of an interchangeable tool handle assembly according to a first exemplary embodiment of the present invention.
Figure 2:
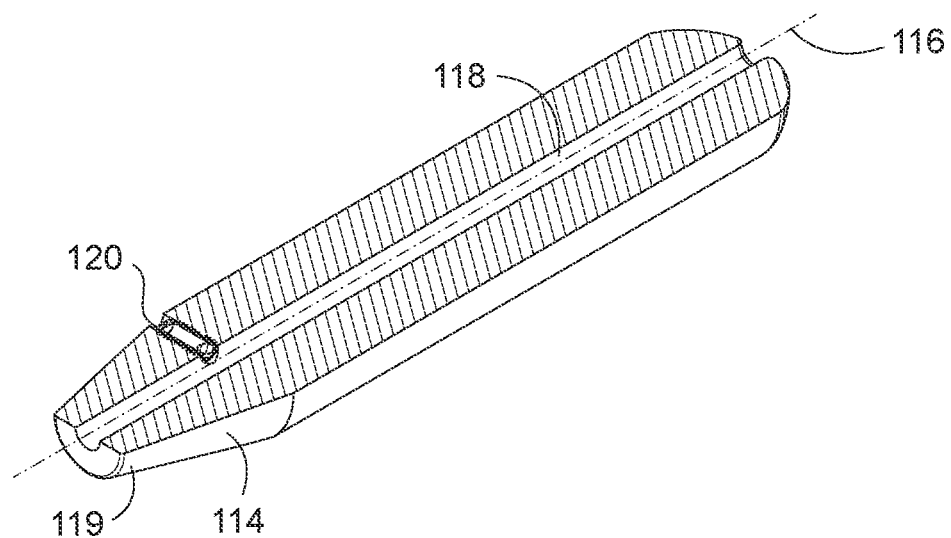
FIG. 2 is a sectional view of the handle assembly of FIG. 1, showing a locking ball assembly.
Figure 3:
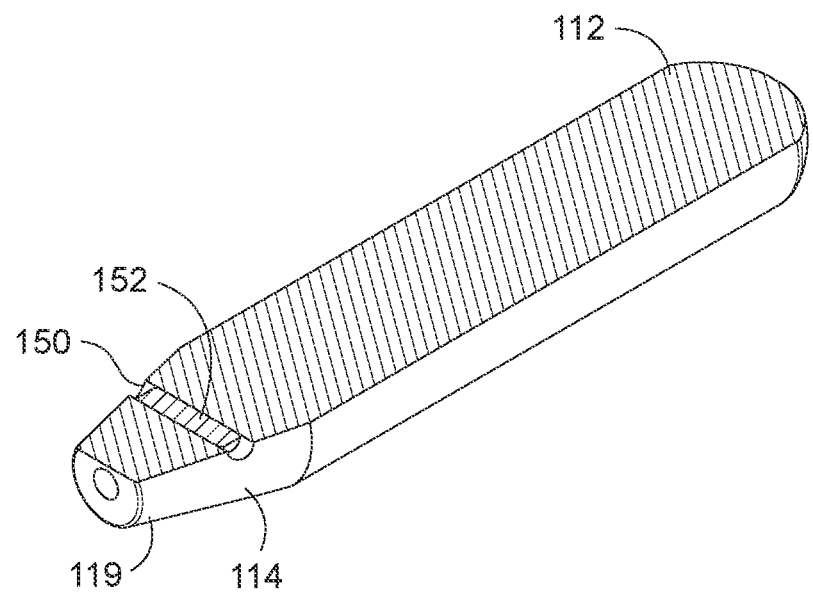
FIG. 3 is a sectional view of the handle assembly of FIG. 1, showing a torque bar.
Figure 4:
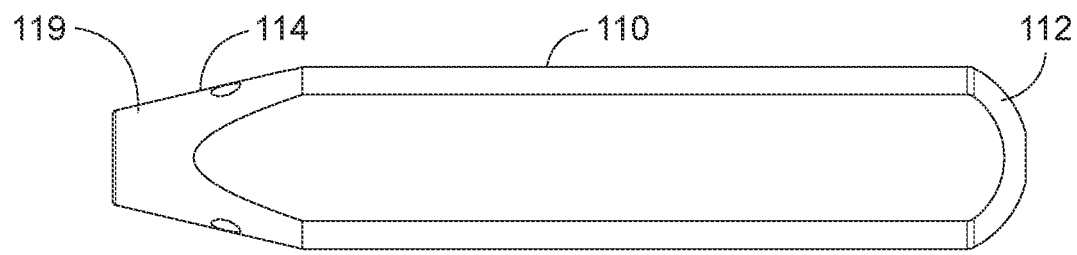
FIG. 4 is a side elevational view of the handle assembly of FIG. 1.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "proximal" means a direction closer to the user and "distal" means a direction farther from the user.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

The invention provides a single use, disposable, and sterile handle assembly as part of a kit with additional instruments and can accommodate multiple different instruments from the kit.

As shown in FIGS. 1-9, a handle assembly 100 ("assembly 100") according to an exemplary embodiment of the invention is shown. Assembly 100 is used to releasably connect to a surgical tool (not shown). Assembly 100 incorporates a ball plunger concept.

Assembly 100 includes an elongate handle body 110 having a proximal end 112, a distal end 114, and a central longitudinal axis 116 extending between proximal end 112 and distal end 114. Body 110 is cannulated, with a generally tubular through-passage 118 extending through body 110 along longitudinal axis 116. Through-passage 118 is sized to allow the shank for a tool (not shown) to be inserted into a distal end 119 of through-passage 118. Body 110 can have a generally square cross-sectional shape, with distal end 119 being tapered.

A side passage 120 is provided through body 110 transverse to longitudinal axis 116 and intersecting through-passage 118. Side passage 120 can be located toward distal end 114, proximate to where distal end 114 begins to taper to distal tip 119. Those skilled in the art, however, will recognize that side passage 120 can be located away from distal end 114. Side passage 120 provides a locking mechanism to releasably retain the shank of a medical tool (not shown) onto assembly 100.

An inner end 122 of side passage 120 is threaded to accept the threads 132 of a screw 130. Screw 130 has a generally hollow body 133 with an outer end 134 having a slot 136 to accept a screwdriver head (not shown) and an inner end 138 containing a ball 140. Inner end 138 is crimped so that ball 140 cannot fall out of body 133.

Figure 5:
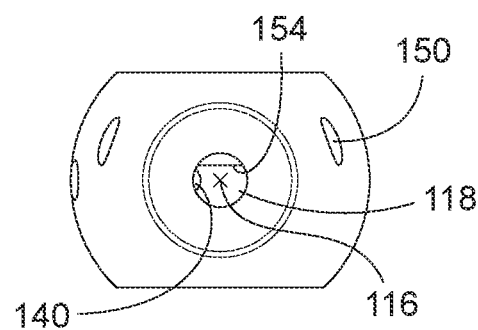
FIG. 5 is a distal end view of the handle assembly of FIG. 1.
Figure 6:
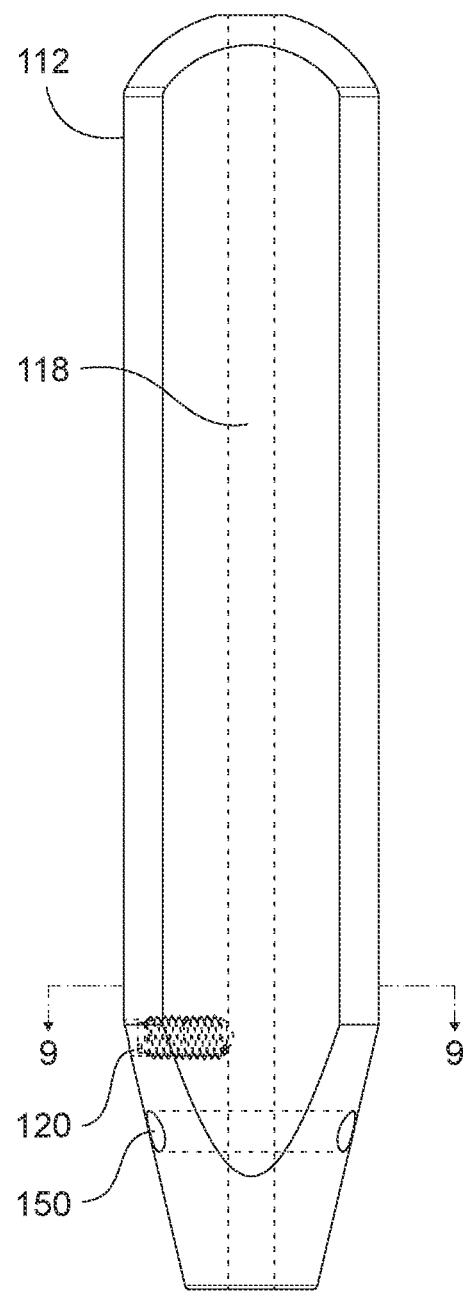
FIG. 6 is a top plan view of the handle assembly of FIG. 1.
Figure 7:
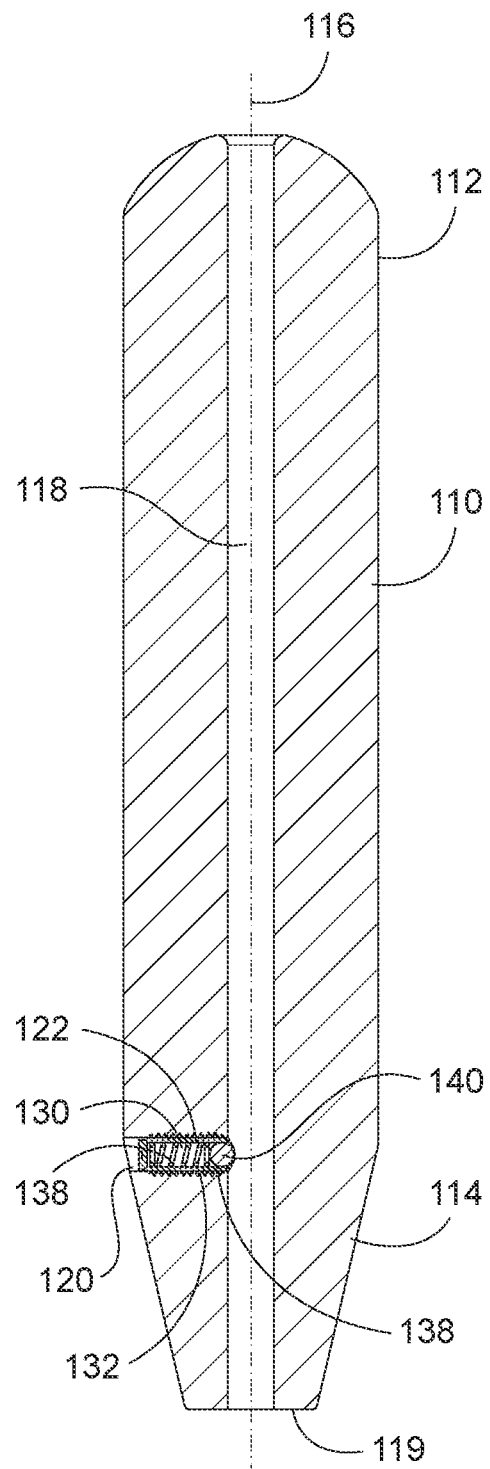
FIG. 7 is a sectional view of the handle assembly of FIG. 6.
Figure 8:
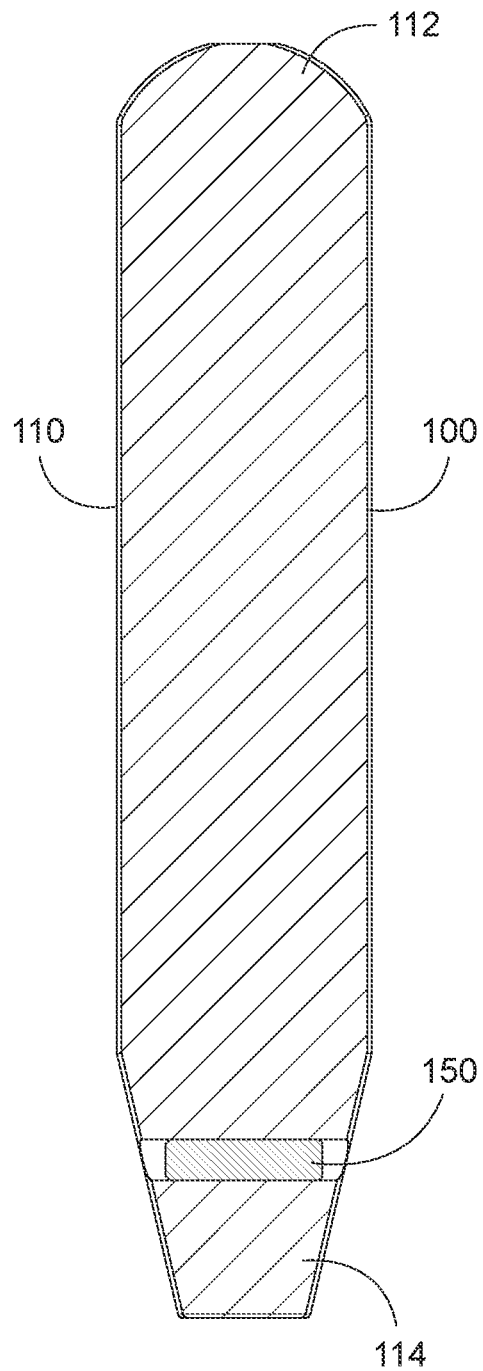
FIG. 8 is a sectional view of the handle assembly if FIG. 6, showing the torque bar.
Figure 9:
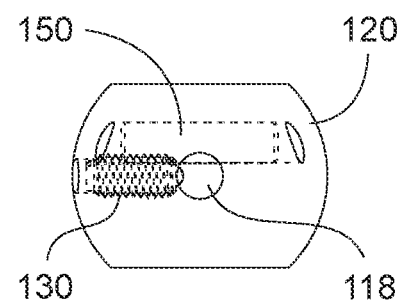
FIG. 9 is a sectional view of the handle assembly of FIG. 6 taken along lines 9-9 of FIG. 6.
Figure 10:
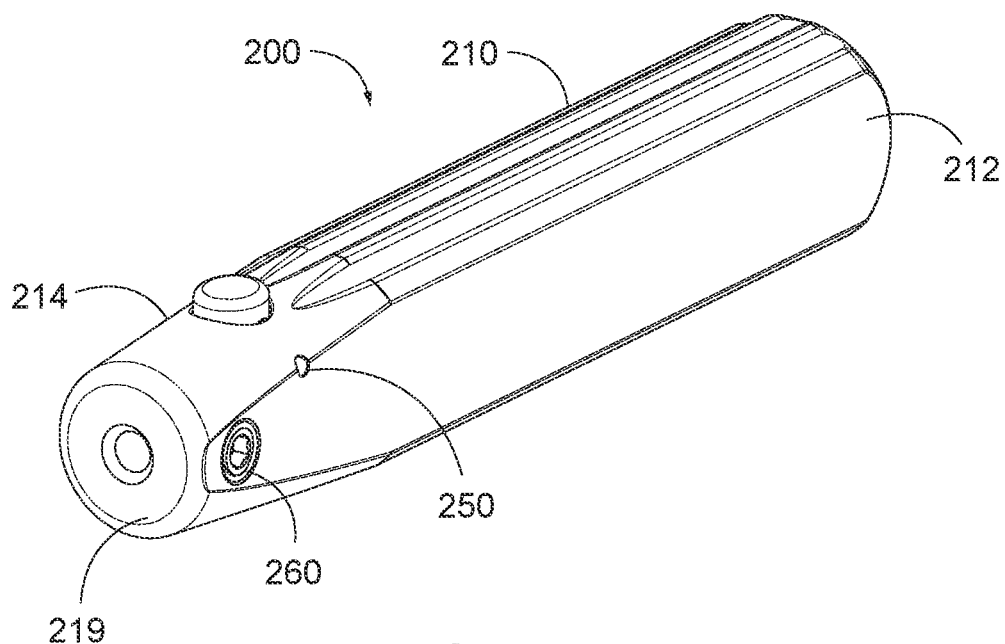
FIG. 10 is a perspective view of an interchangeable tool handle assembly according to a second exemplary embodiment of the present invention.
Figure 11:
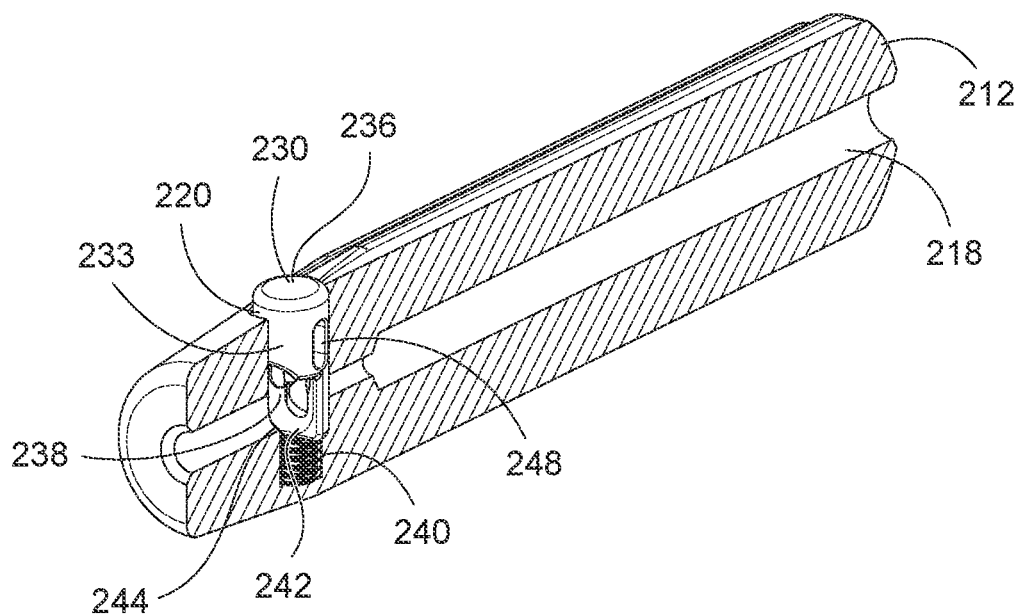
FIG. 11 is a sectional view of the handle assembly of FIG. 10, showing a retaining assembly.
Figure 12:
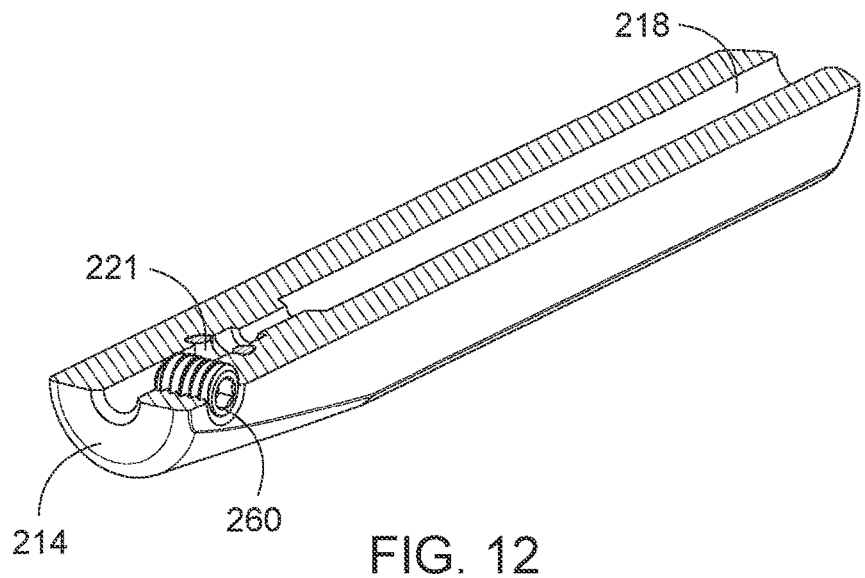
FIG. 12 is a sectional view of the handle assembly of FIG. 10, showing a set screw.
Figure 13:
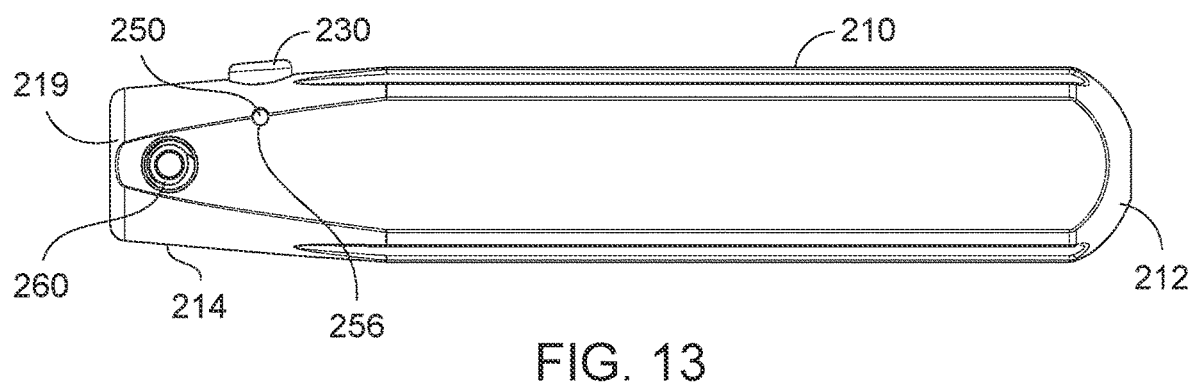
FIG. 13 is a side elevational view of the handle assembly of FIG. 10.
Figure 14:
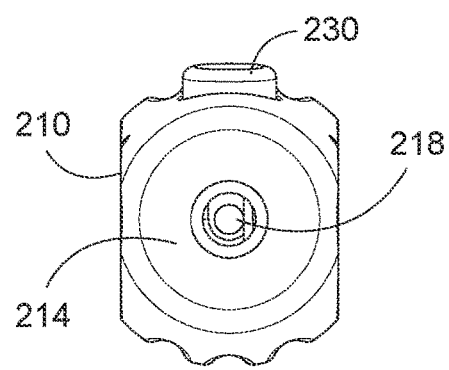
FIG. 14 is a distal end view of the handle assembly of FIG. 10.

Screw 130 also includes a biasing member 138, such as a helical spring, inside body 133 such that biasing member 138 biases ball 140 out of body 133. When screw 130 is fully screwed into side passage 120, ball 140 extends into through-passage 118, as shown in FIG. 5, and biases the shank against the far wall of through-passage 118, retaining the shank in assembly 100. To remove the shank, a user must pull on the shank, which dislocates ball 140 into hollow body 133, allowing the shank to be removed from assembly 100.

A transverse passage 150 is formed in distal end 114, generally parallel to side passage 120. Transverse passage 150 is located such that a lower central portion of transverse passage 150 is in communication with through-passage 118. A pin 152 is inserted into transverse passage 150 such that a portion 154 of pin 152 extends into through-passage 118. Portion 154 engages a flat (not shown) on the shank of the tool and prevents the shank from rotating within through-passage 118, effectively acting as a torque transmitter from handle body 110 to the tool.

As shown in FIGS. 10-20, a handle assembly 200 ("assembly 200") according to an alternative exemplary embodiment of the invention is shown. Assembly 200 is used to releasably connect to a surgical tool (not shown). Assembly 200 incorporates a center button concept.

Figure 15:
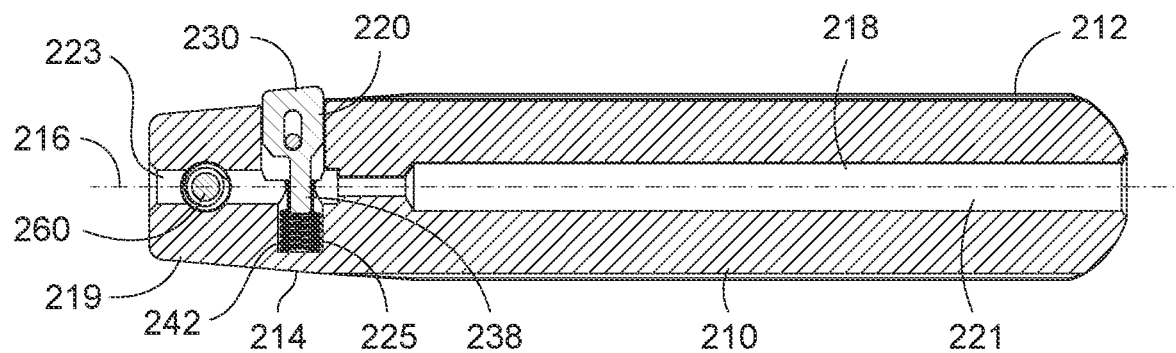
FIG. 15 is a sectional view of the handle assembly of FIG. 10.
Figure 16:
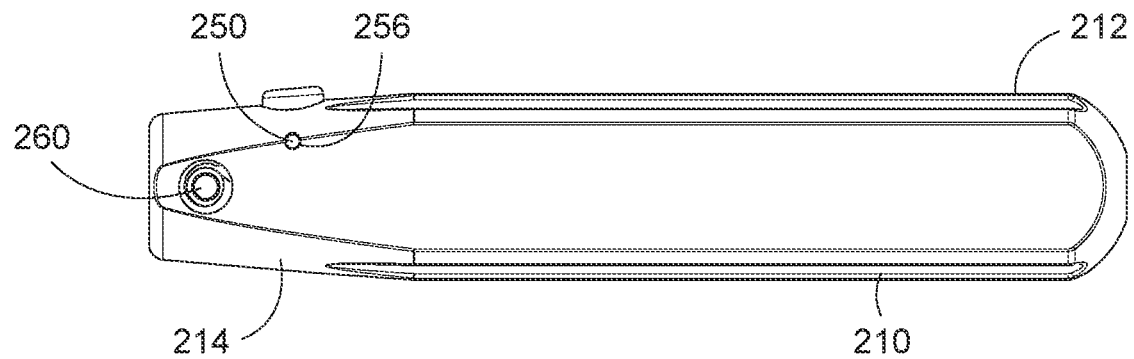
FIG. 16 is a side elevational view of the handle assembly of FIG. 10.
Figure 17:
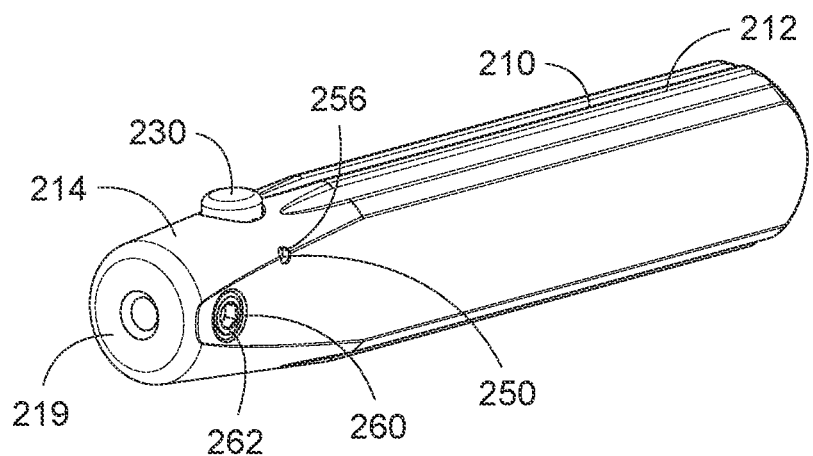
FIG. 17 is a perspective view of the handle assembly of FIG. 10.

Assembly 200 includes an elongate handle body 210 having a proximal end 212, a distal end 214, and a central longitudinal axis 216 extending between proximal end 212 and distal end 214. Body 210 is cannulated, with a generally tubular through-passage 218 extends through body 210 along longitudinal axis 216. Through-passage 218 is sized to allow the shank for a tool (not shown) to be inserted into distal end 214 of through-passage 218. As shown in FIG. 15, a proximal end 221 of through-passage 218 can have a larger diameter than a distal end 223 of through-passage 218. Body 210 can have a generally square cross-sectional shape, with a tapered distal tip 219 at distal end 214.

A side passage 220 is provided through body 210 transverse to longitudinal axis 216, intersecting through-passage 218, and extending beyond through-passage 218, but not entirely through body 210, thereby forming a blind passage 225. Side passage 220 can be located toward distal end 214, proximate to where distal end 214 begins to taper to distal tip 219. Those skilled in the art, however, will recognize that side passage 220 can be located away from distal end 214. Side passage 220 provides a locking mechanism to releasably retain the shank of a medical tool (not shown) onto assembly 200.

A retaining member 230 has a generally cylindrical body 233 with an outer end 234 having a push button 236 and an inner end 238 having a slot 240 formed therethrough. Slot 240 is axially aligned with through-passage 218. A biasing member 242, in the form of a helical spring, is located in blind passage 225 and biases retaining member 230 outward from side passage 230. A stop portion 244 of inner end 238 of retaining member 230 engages biasing member 244.

Push button 236 includes an elongate slot 248 extending therethrough generally orthogonally and above through-passage 218. Additionally, body 210 includes a passage 250 axially aligned with elongate slot 248 such that a retaining pin 256 is slid through passage 250, through elongate slot 248, and into a corresponding through passage (not shown) such that retaining pin 256 retains retaining member 230 in side passage 220, yet allows push button 236 to travel the length of elongate slot 248 between the position shown in FIG. 19 and the position shown in FIG. 20.

Figure 18:
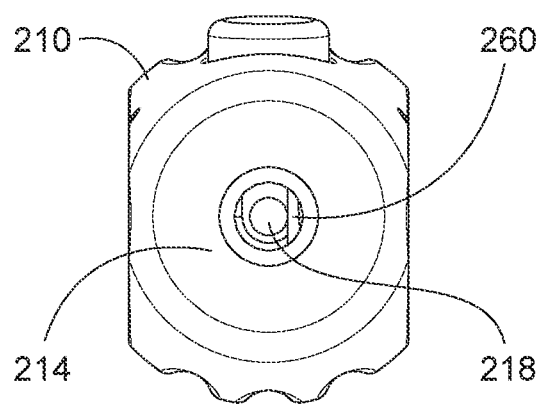
FIG. 18 is a distal end view of the handle assembly of FIG. 10.
Figure 19:
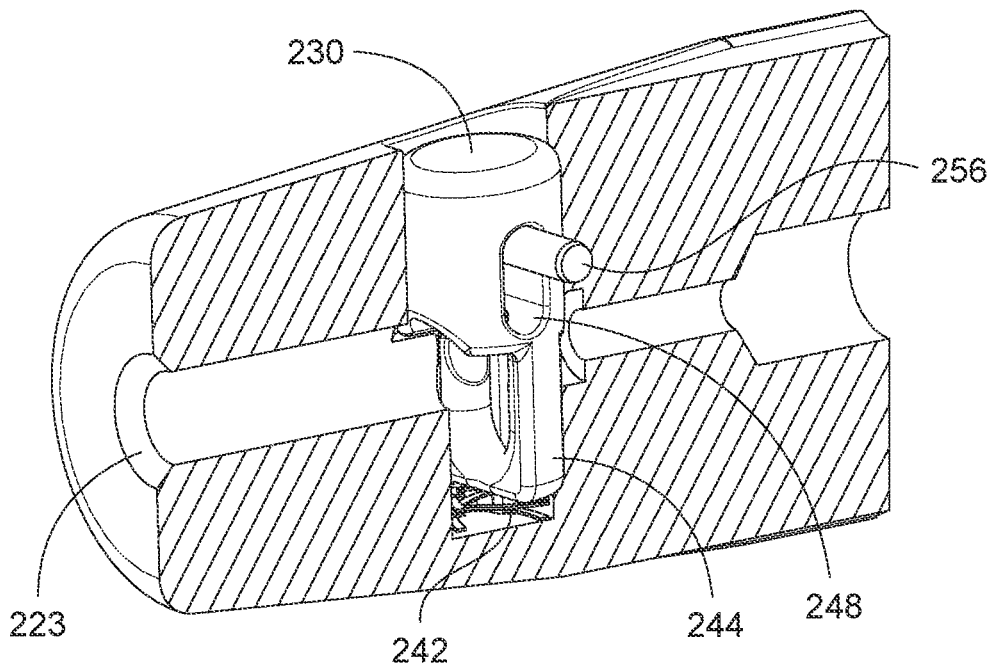
FIG. 19 is a perspective view, in section, showing the pushbutton in a depressed position.
Figure 20:
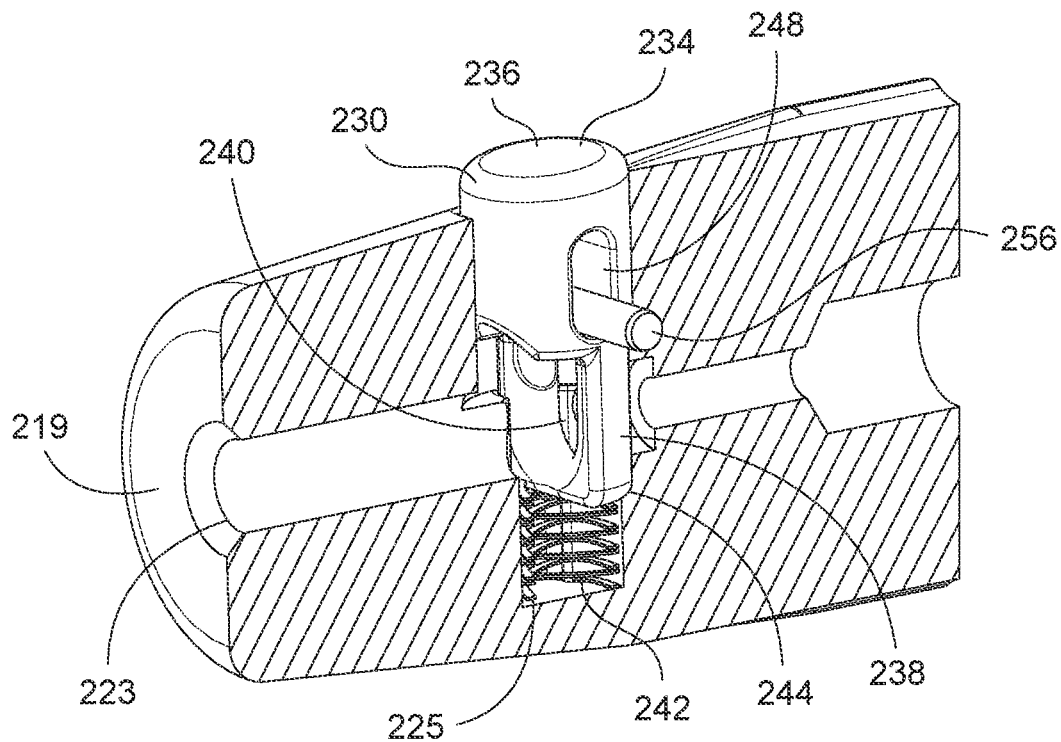
FIG. 20 is a perspective view, in section, showing the pushbutton in an undepressed position.
Figure 21:
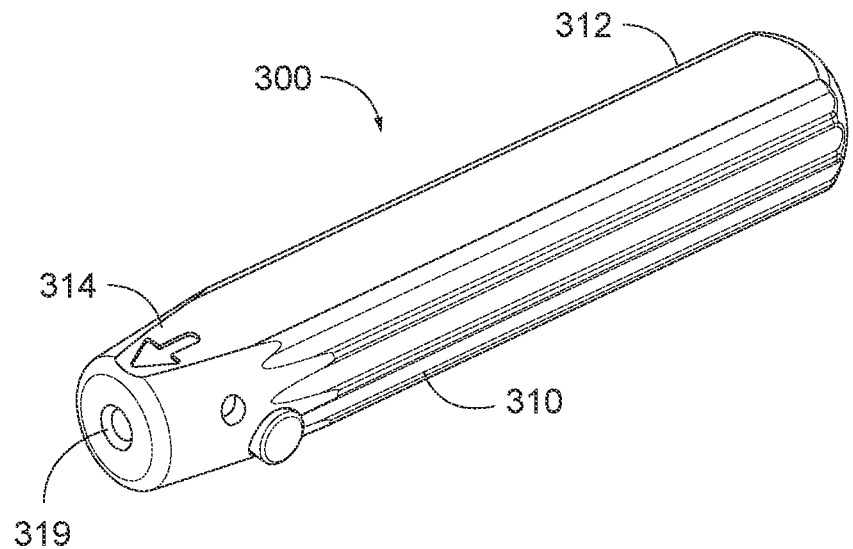
FIG. 21 is a perspective view of an interchangeable tool handle assembly according to a third exemplary embodiment of the present invention.
Figure 22:
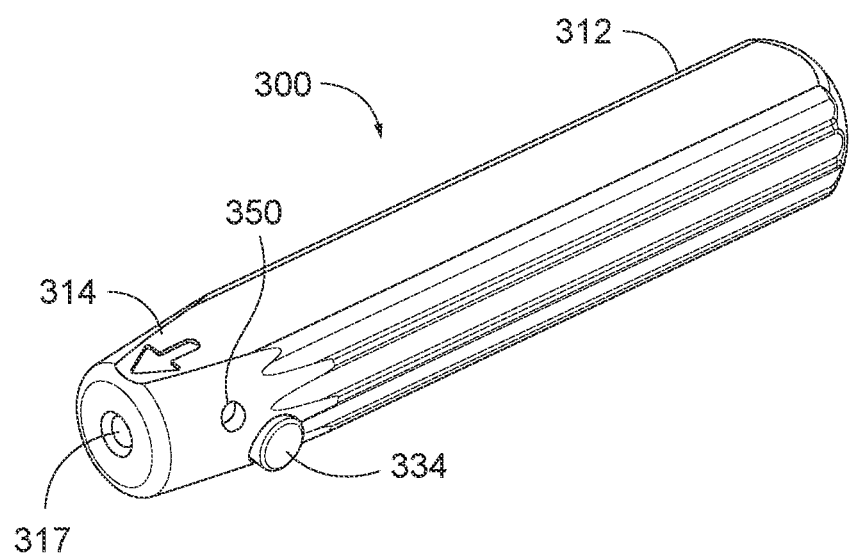
FIG. 22 is a perspective line drawing view of the handle assembly of FIG. 21.
Figure 23:
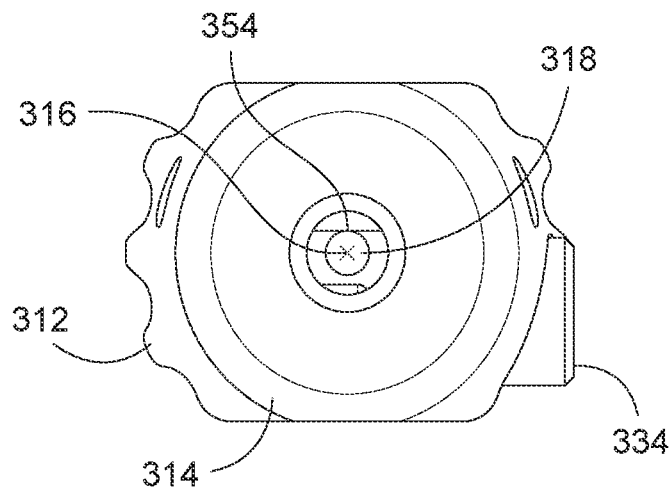
FIG. 23 is a distal end view of the handle assembly of FIG. 211.
Figure 24:
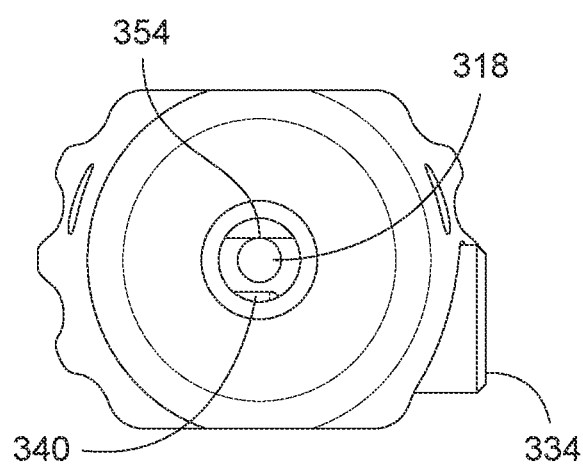
FIG. 24 is a distal end line drawing view of the handle assembly of FIG. 21.

A securing member in the form of a set screw 260 is threadingly inserted into a threaded opening 262 in body 210, between push button 236 and distal tip 219, generally 90 degrees around body 210 from side passage 220. Set screw 260 can be screwed into body 210 such that set screw 260 extends into through-passage 218, as shown in FIG. 18.

When push button 236 is depressed into side passage 220, stop portion 244 of inner end 238 biases biasing member 242 into blind passage 225 and slot 240 aligns with through-passage 218, allowing the shank (not shown) of a medical device to be inserted into through-passage 218 from distal tip 219.

After the shank is fully inserted, push button 236 is released and biasing member 242 biases push button 236 upward so that stop portion 244 engages the shank and urges the shank against the side of through-passage 218. If the shank has a flat, the shank can be rotated such that the flat faces set screw 260. Set screw 260 can be screwed into threaded opening 262 until set screw 260 engages the flat and urges the shank against the side wall of through-passage 218. This arrangement transfers torque from handle body 210 to the shank for rotation of the tool when handle body 210 is rotated.

As shown in FIGS. 21-27, a handle assembly 300 ("assembly 300") according to an alternative exemplary embodiment of the invention is shown. Assembly 300 is used to releasably connect to a surgical tool (not shown). Assembly 300 incorporates an off-center button concept.

Assembly 300 includes an elongate handle body 310 having a proximal end 312, a distal end 314, and a central longitudinal axis 316 extending between proximal end 312 and distal end 314. Body 310 is cannulated, with a generally tubular through-passage 318 extending through body 310 along longitudinal axis 316. Through-passage 318 is sized to allow the shank for a tool (not shown) to be inserted into a distal end 317 of through-passage 318. Body 310 can have a generally square cross-sectional shape, with a tapered distal tip 321 at distal end 314.

A side passage 320 is provided through body 310 transverse to longitudinal axis 316, intersecting a bottom part of through-passage 318 and therefore offset from its longitudinal axis 316, and extending beyond through-passage 318, but not entirely through body 310, narrowing to form a blind passage 319. Side passage 320 can be located toward distal end 314, proximate to where distal end 314 begins to taper to distal tip 321. Those skilled in the art, however, will recognize that side passage 320 can be located away from distal end 314. Side passage 320 provides a locking mechanism to releasably retain the shank of a medical tool (not shown) onto assembly 300.

A retaining member 330 has a generally cylindrical body 333 with an outer end 334 having a push button 336 and an inner end 338 having a plunger 340. A biasing member 344, in the form of a helical spring, is located in blind passage 319 and biases retaining member 330 outward from side passage 330. Plunger 340 engages biasing member 344. A thin shaft 345 connects push button 336 and plunger 340.

Figure 26:
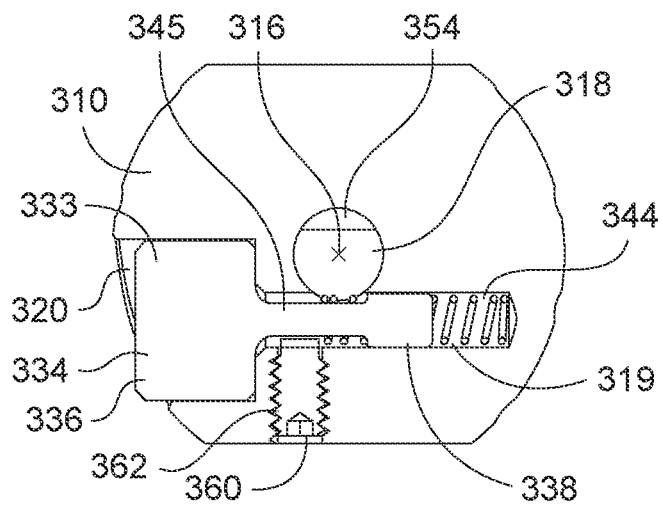
FIG. 26 is a sectional view of the handle assembly of FIG. 21, showing the pushbutton in an undepressed position.
Figure 27:
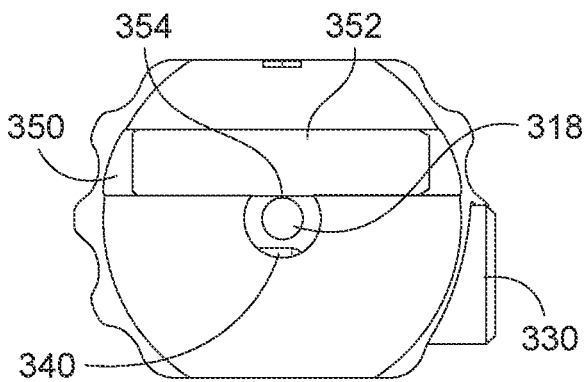
FIG. 27 is a sectional view of the handle assembly of FIG. 21, showing the torque bar.

A securing member in the form of a set screw 360 is threadingly inserted into a threaded opening 362 in body 310, generally 90 degrees around body 310 from side passage 320. Set screw 360 can be screwed into body 310 such that set screw 360 extends into side passage 320, as shown in FIG. 26. Set screw 360 is located along the length of thin shaft 345 between push button 336 and plunger 340 to engage plunger 340 and prevent retaining member 330 from being able to be removed from body 310.

A transverse passage 350 is formed in distal end 314, generally parallel to side passage 320. Transverse passage 350 is located such that a lower central portion of transverse passage 350 is in communication with through-passage 318.

A pin 352 is inserted into transverse passage 350 such that a portion 354 of pin 352 extends into through-passage 318. Portion 354 engages a flat (not shown) on the shank of the tool and prevents the shank from rotating within through-passage 318, effectively acting as a torque transmitter from handle body 310 to the tool.

Figure 25:
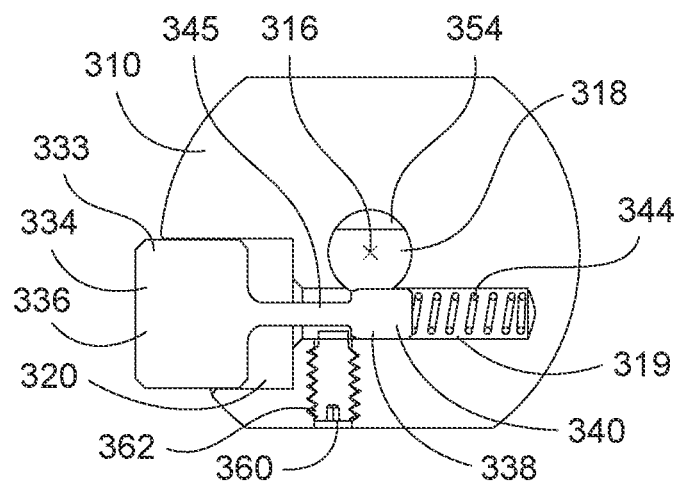
FIG. 25 is a sectional view of the handle assembly of FIG. 21, showing the pushbutton in a depressed position.

When push button 336 is depressed into side passage 320 to the position shown in FIG. 25, plunger 340 biases biasing member 344 into blind passage 319 and thin shaft 345 aligns with through-passage 318, allowing the shank (not shown) of a medical device to be inserted into through-passage 318 from distal tip 321.

After the shank is fully inserted, push button 336 is released as shown in FIG. 26 and biasing member 344 biases push button 336 outward so that plunger 340 engages the shank and urges the shank against the side of through-passage 318. If the shank has a flat, the shank can be rotated such that the flat faces portion 354 of pin 352. This arrangement transfers torque from handle body 310 to the shank for rotation of the tool when handle body 310 is rotated.

While balls and spring biased securing mechanisms are disclosed for releasably retaining a tool in through-passages 118, 218, 318, those skilled in the art will recognize that other mechanisms, such as, for example, a spring clip, clasp or other deformable level, can be used to displace and deform the tool shank to secure the tool shank in any one of through-passages 118, 218, 318.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A handle assembly comprising:
   an elongate body having a proximal end, a distal end, and a central longitudinal axis extending between the proximal end and the distal end;
   a through-passage extending along the central longitudinal axis between the proximal end and the distal end wherein the proximal end and the distal end of the body are open such that the through-passage extends the length of the entire assembly;
   a side passage extending through the body transverse to the longitudinal axis, the side passage having a side passage longitudinal axis extending orthogonal to the longitudinal axis, the side passage intersecting the through-passage, the side passage extending along either side of the through-passage, and the side passage longitudinal axis being offset from and not intersecting the central longitudinal axis; and
   a locking mechanism located in the side passage and configured to releasably retain a medical tool onto the assembly.

2. The handle assembly according to claim 1, wherein the side passage comprises a threaded inner end and a screw threadingly inserted into the threaded inner end.

3. The handle assembly according to claim 2, wherein the screw has a generally hollow body with an outer end having a slot formed therein.

4. The handle assembly according to claim 2, wherein the screw includes an inner end containing a ball.

5. The handle assembly according to claim 4, wherein, when the screw is fully screwed into the side passage, the ball extends into through passage.

6. The handle assembly according to claim 2, wherein the side passage extends beyond the through-passage, but not entirely through the body, thereby forming a blind passage.

7. The handle assembly according to claim 6, further comprising a retaining member inserted into the side passage, the retaining member having a generally cylindrical body with an outer end having a push button and an inner end having a slot formed therethrough, wherein the slot is axially aligned with the through-passage.

8. The handle assembly according to claim 7, further comprising a biasing member located in the blind passage such that the biasing member biases the retaining member outward from the side passage.

9. The handle assembly according to claim 7, wherein the push button includes an elongate slot extending therethrough generally orthogonally and above the through-passage.

10. The handle assembly according to claim 9, further comprising a passage axially aligned with the elongate slot such that a retaining pin extends through the passage and through the elongate slot such that the retaining pin retains the retaining member in the side passage.

11. The handle assembly according to claim 6, further comprising a retaining member having a generally cylindrical body having an outer end, an inner end, and a shaft, thinner than each of the inner end and the outer end, connecting the inner end to the outer end.

12. The handle assembly according to claim 11, further comprising a member insertable into the side passage between the outer end of the body and the inner end of the body.

13. The handle assembly according to claim 11, wherein the retaining member is movable between a first position wherein a portion of the inner end extends into the through-passage and a second position wherein the portion of the inner end does not extend into the through-passage.

14. The handle assembly according to claim 1, further comprising a transverse passage in the distal end, generally parallel to the side passage such that a lower central portion of the transverse passage is in communication with the through-passage.

15. The handle assembly according to claim 14, further comprising a pin inserted into the transverse passage such that a portion of the pin extends into the through-passage.

16. The handle assembly according to claim 15, wherein the portion is configured to engage a flat on a shank of a tool and to prevent the shank from rotating within the through-passage.

17. The handle assembly according to claim 1, wherein a proximal end of the through-passage has a larger diameter than a distal end of the through-passage.

18. A handle assembly comprising:
   an elongate body having a proximal end, a distal end, and a central longitudinal axis extending between the proximal end and the distal end;
   a through-passage extending along the central longitudinal axis between the proximal end and the distal end, wherein the proximal end and the distal end of the body are open such that the through-passage extends the length of the entire assembly;
   a side passage extending orthogonal to the through-passage;
   a locking mechanism located in the side passage and configured to releasably retain a medical tool onto the assembly; and
   a retaining member adapted to engage the locking mechanism and retain the locking mechanism in the side passage, the retaining member having a biasing member configured to bias the locking mechanism to a medical tool retaining position.

19. The handle assembly according to claim 18, wherein the locking mechanism comprises a biasing member configured to move the locking mechanism between a locking and an unlocking position.

20. The handle assembly according to claim 18, wherein the retaining member is insertable into the through-passage distal of the locking mechanism.

\* \* \* \* \*